US012226474B2

United States Patent
Hibner

(10) Patent No.: US 12,226,474 B2
(45) Date of Patent: *Feb. 18, 2025

(54) METHODS AND COMPOSITIONS FOR TREATING INFECTIONS

(71) Applicant: Decoy Therapeutics Inc., Cambridge, MA (US)

(72) Inventor: Barbara L. Hibner, Winchester, MA (US)

(73) Assignee: Decoy Therapeutics Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,681

(22) Filed: Jan. 18, 2022

(65) Prior Publication Data

US 2022/0233683 A1 Jul. 28, 2022

Related U.S. Application Data

(60) Provisional application No. 63/140,387, filed on Jan. 22, 2021.

(51) Int. Cl.
*A61K 39/215* (2006.01)
*A61K 39/00* (2006.01)

(52) U.S. Cl.
CPC .... *A61K 39/215* (2013.01); *A61K 2039/6018* (2013.01); *A61K 2039/627* (2013.01)

(58) Field of Classification Search
CPC .......... A61K 39/215; A61K 2039/6018; A61K 2039/627; C07K 14/165
See application file for complete search history.

(56) References Cited

U.S. PATENT DOCUMENTS

| | | | |
|---|---|---|---|
| 10,172,961 B2 | 1/2019 | Porotto et al. | |
| 11,180,534 B1 | 11/2021 | Bond et al. | |
| 2012/0028887 A1 | 2/2012 | Shai et al. | |
| 2015/0175666 A1 | 6/2015 | Shai et al. | |
| 2017/0216448 A1 | 8/2017 | Porrotto et al. | |

FOREIGN PATENT DOCUMENTS

| | | | | |
|---|---|---|---|---|
| WO | WO-2005002500 A2 * | 1/2005 | .......... | C07K 14/005 |
| WO | 2021046398 A2 | 3/2021 | | |
| WO | 2021178971 A1 | 9/2021 | | |
| WO | 2021195401 A1 | 9/2021 | | |
| WO | 2021207517 A2 | 10/2021 | | |
| WO | WO-2022081711 A1 * | 4/2022 | .......... | A61K 47/542 |
| WO | WO-2023150375 A2 * | 8/2023 | | |

OTHER PUBLICATIONS

Duquerroy S, Vigouroux A, Rottier PJ, Rey FA, Bosch BJ. Central ions and lateral asparagine/glutamine zippers stabilize the post-fusion hairpin conformation of the SARS coronavirus spike glycoprotein. Virology. May 10, 2005;335(2):276-85. (Year: 2005).*
Yan Z, Tripet B, Hodges RS. Biophysical characterization of HRC peptide analogs interaction with heptad repeat regions of the SARS-coronavirus Spike fusion protein core. J Struct Biol. Aug. 2006;155(2):162-75. Epub Apr. 27, 2006. (Year: 2006).*
Guo L, Lin S, Chen Z, Cao Y, He B, Lu G. Targetable elements in SARS-CoV-2 S2 subunit for the design of pan-coronavirus fusion inhibitors and vaccines. Signal Transduct Target Ther. May 10, 2023;8(1):197. (Year: 2023).*
Outlaw VK, Bovier FT, Mears MC, et al. Inhibition of Coronavirus Entry In Vitro and Ex Vivo by a Lipid-Conjugated Peptide Derived from the SARS-CoV-2 Spike Glycoprotein HRC Domain. mBio. Oct. 20, 2020;11(5):e01935-20. (Year: 2020).*

* cited by examiner

*Primary Examiner* — Rachel B Gill
(74) *Attorney, Agent, or Firm* — Elmore Patent Law Group, P.C.; Carolyn S. Elmore; Jia Kang

(57) ABSTRACT

The invention provides a compound comprising one, two, three or more non-natural HRC sequence of a viral spike peptide conjugated to a hydrophobic moiety via an optional linker. The hydrophobic moiety can be a membrane integrating ligand, such as a cholesterol, a sphingolipid, a glycolipid, a glycerophospholipid. The non-natural viral spike peptide is preferably a coronavirus spike protein characterized by one or more D-amino acids. The peptides of the invention inhibit viral fusion. The invention includes compositions for the delivery of compounds of the invention, such as pulmonary or nasal delivery. The invention also provides a method of treating or preventing a viral infection, including for example a SARS-COV-2 (COVID-19) infection, in a subject in need thereof comprising administering an effective amount of a compound of the invention.

7 Claims, 3 Drawing Sheets
Specification includes a Sequence Listing.

SEQUENCE LISTING

```
<160> NUMBER OF SEQ ID NOS: 2

<210> SEQ ID NO 1
<211> LENGTH: 36
<212> TYPE: PRT
<213> ORGANISM: Homo sapiens

<400> SEQUENCE: 1

Asp Ile Ser Gly Ile Asn Ala Ser Val Val Asn Ile Gln Lys Glu Ile
1               5                   10                  15
```

```
Asp Arg Leu Asn Glu Val Ala Lys Asn Leu Asn Glu Ser Leu Ile Asp
            20                  25                  30

Leu Gln Glu Leu
        35

<210> SEQ ID NO 2
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: D-amino acid

<400> SEQUENCE: 2

Ile Gly Ser Ile Asp Asn Ala Ser Val Val Asn Ile Gln Lys Glu Ile
1               5                   10                  15

Asp Arg Leu Asn Glu Val Ala Lys Asn Leu Asn Glu Ser Leu Ile Asp
            20                  25                  30

Leu Gln Glu Leu
        35
```

METHODS AND COMPOSITIONS FOR TREATING INFECTIONS

RELATED APPLICATION

This application claims the benefit of priority to U.S. Application No. 63/140,387 filed on Jan. 22, 2021, which is incorporated herein by reference.

SEQUENCE LISTING

The sequence listing submitted via EFS, in compliance with 37 CFR § 1.52 (e) (5), is incorporated herein by reference. The sequence listing XML file submitted via EFS contains the file "43143000 US1.xml", created on Jun. 9, 2023, which is 3,216 bytes in size.

BACKGROUND OF THE INVENTION

A variety of viruses are known to cause respiratory infections in humans, resulting in illnesses that are typically classified according to their clinical presentation, such as the common cold, influenza, bronchiolitis, croup or pneumonia. Such infections are generally self-limiting, but in certain patients, notably the elderly, infants, and those with compromised immune systems, can lead to more severe disease, including pneumonia, which can be life threatening. Most medications prescribed for these diseases provide only relief of symptoms, and there are few available drugs which modify the course of any of these diseases. In addition, new respiratory diseases caused by zoonotic viruses have recently emerged, including Severe Acute Respiratory Syndrome coronavirus (SARS-COV), identified in 2002, Middle East Respiratory Syndrome coronavirus (MERS-COV), identified in 2012, and, most recently, Severe Acute Respiratory Syndrome coronavirus-2 (SARS-COV-2), which was first described in December 2019 and causes a disease referred to as COVID-19. The SARS-COV-2 virus remains a global threat. SARS-COV and MERS-COV are not presently a danger to human populations but may exist in animal reservoirs with the potential to threaten humans in the future.

There remains a need in the art for methods of treating or preventing viral respiratory infections.

SUMMARY OF THE INVENTION

The present invention provides compounds, compositions and methods of use thereof for treating or preventing an infection.

In one embodiment, the invention provides a compound comprising one, two, three or more non-natural HRC sequence of a viral spike peptide conjugated to a hydrophobic moiety via an optional linker. The hydrophobic moiety can be a membrane integrating ligand, such as a cholesterol, a sphingolipid, a glycolipid, a glycerophospholipid. The non-natural viral spike peptide is preferably a coronavirus spike protein characterized by one or more D-amino acids. The peptides of the invention inhibit viral fusion. The optional linker is a bivalent or multivalent moiety that covalently bonds to the HRC sequence and the hydrophobic moiety. A preferred linker is a polyethylene glycol-containing linker. The invention includes compositions for the delivery of compounds of the invention, such as pulmonary or nasal delivery. The invention also provides a method of treating or preventing a viral infection, including for example a SARS-CoV-2 (COVID-19) infection, in a subject in need thereof comprising administering an effective amount of a compound of the invention. The invention further provides methods of producing the compositions of the invention.

A preferred compound of the invention has the formula:

Ac−DISGINASVVNIQKEIDRLNEVAKNLNESLIDLQEL−GSGSG−NH−[linker with maleimide-PEG₄-cholesterol conjugate]

Ac−DISGINASVVNIQKEIDRLNEVAKNLNESLIDLQEL−GSGSG−NH−[linker]

wherein the peptides include at least one Retro-inversion (RI) peptide.

DETAILED DESCRIPTION OF THE INVENTION

Compounds of the invention can be characterized by the following general formula:

(Peptide-Linker)$_n$-B-Hydrophobic Moiety

Wherein n is an integer selected from 1, 2, 3 or more.

Each Peptide is independently and preferably a non-natural HRC peptide derived from a coronavirus spike protein. While preferred embodiments of the invention utilize non-natural peptides, native or wild-type peptides can be used as well. The so-called HRC peptide or region of the coronavirus spike protein is preferred. The HRC peptides inhibit viral fusion, an important early step in the infection process. The wild type HRC peptide is a conserved region of the spike, or S, protein across coronaviruses and is described in Xia et al., Cell Research (2020) 30:343-355, Xia et al., Sci. Adv. 2019, 5: eaav4580 10 Apr. 2019, and characterized in Duquerroy et al, Virology (2005) 335:276-285, which are incorporated herein by reference in their entirety.

The conserved nature of the fusion regions (HRC/HRN) and mechanism of the class I enveloped viruses make it an ideal target to develop a pan-coronavirus inhibitor.

Preferred wild type HRC peptides comprise the sequence and binding fragments thereof:

```
                                        (SEQ ID NO. 1)
DISGINASVVNIQKEIDRLNEVAKNLNESLIDLQEL
```

With regard to the HRC peptide in SEQ ID NO.1, the conventional numbering of the amino acids begins with 1150 at D. 1151I, 1154I and 1158V are in the hydrophobic interface pre-fusion and 1159V is exposed. These amino acids stabilize a helix. When the conformation change occurs (e.g., protease clipping to release FP, 1158V is exposed and 1159 V presents in the hydrophobic surface interacting with HRN trimer. 1155N, and 1176N are implicated in N-linked glycosylation conserved in coronavirus. The first 7 amino acids are implicated in HRN binding. The "N-Cap" region spans 1159V and 1171V. The 1171V is a conserved hydrophobe in coronaviruses and stabilizes the HRC hydro-core and is involved in the HRN interaction.

Figure 1:
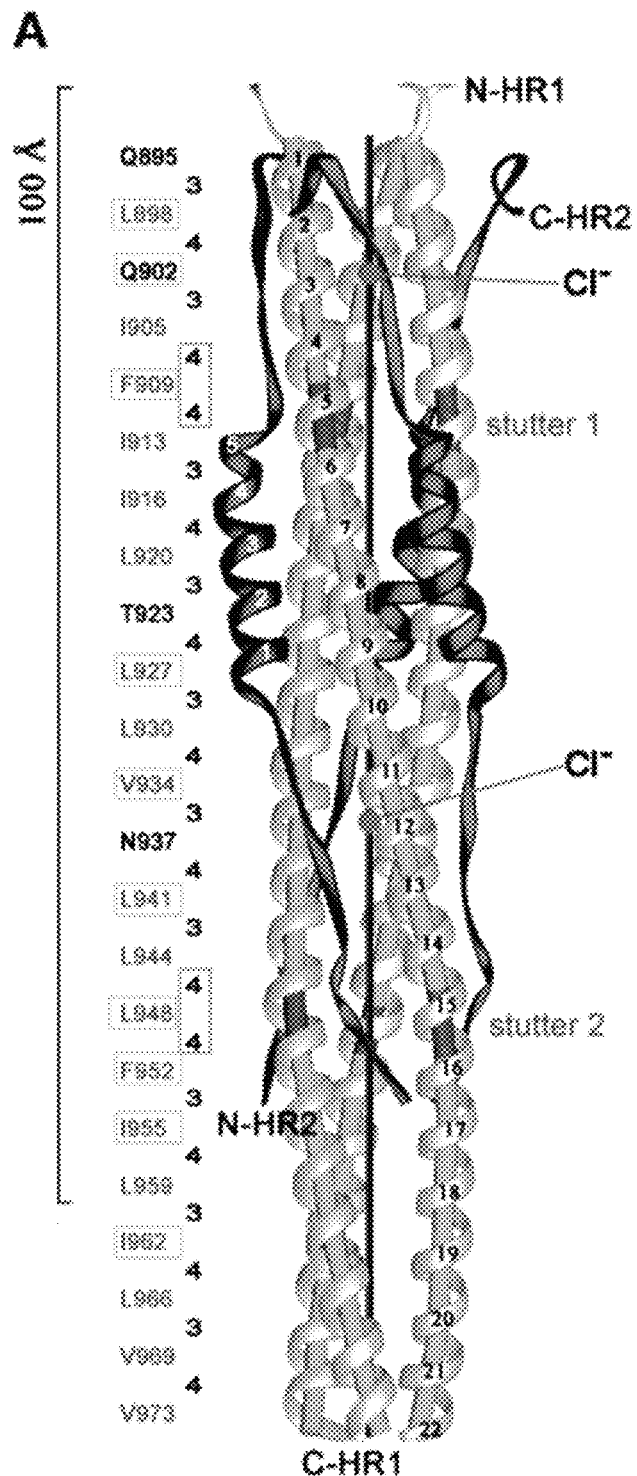
FIG. 1 is model of the HRC peptide from a coronavirus as described in Duquerroy et al, Virology (2005) 335:276-285.
Figure 2:
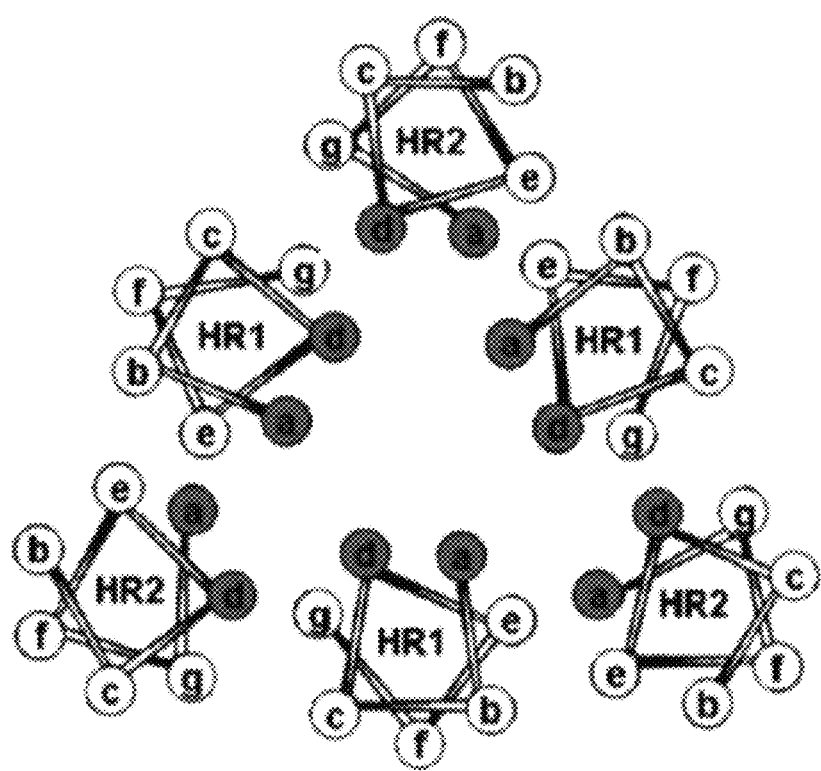
FIG. 2 is a cross section view of an S protein trimer.

The hydrophobic core spans 1161I and 1175L and is helical pre- and post-fusion. The isoleucines, leucines and alanine are important in folding and stability of a coiled coil. The C-Cap region spans 1176N and 1185L. 1179L, 1182L and 1185L are in the hydrophobic interface pre-fusion and 1180I is exposed. These amino acids stabilize the helix. 1185Y may be implicated in hydrophobic packing between three polypeptide chains in a trimeric coiled coil. When confirmation change occurs (protease clipping to release FP), 1179L is exposed and 1180I is in the hydrophobic surface interacting with a HRN trimer. 1164E and 1184E form a salt bridge between HRC and HRN. Further, 1159V, 1160N, 1171V and 1180I have been shown to interact with HRN in crystal structures. A cross section view of an S protein trimer can be illustrated in FIG. 2.

Preferred Peptides are selected from variants of a wild type HRC peptides comprise the sequence and binding fragments thereof:

```
                                        (SEQ ID NO. 1)
DISGINASVVNIQKEIDRLNEVAKNLNESLIDLQEL.
```

For example, the wild type HRC sequence can include 1, 2, 3, 4, 5, 6, 7, 8, 9, 10 or more additional amino acids native to the S protein at the N- and/or C termini. For example, glycine can be added to the N-terminus. Additionally, the wild type HRC peptide fragment can delete 1, 2, 3, 4, 5, 6, 7, 8, 9, or 10 amino acids at the N and/or C termini and inhibit infection. Typically, not more than ten total amino acids are deleted in total. For example, the 10 amino acids at the C terminus can be deleted and be expected to retain inhibitory activity.

Variants of the wild type HRC peptide can also be used. The term "variant" is defined as a peptide which has at least one amino acid deleted, added, or substituted in comparison with a wild type sequence, such as SEQ ID NO. 1 or other native sequence described herein. Variants preferably bind the cognate ligand of the wild type sequence. For example, a peptide wherein 1, 2, 3, 4 or 5 amino acids of SEQ ID NO. 1 are substituted can be used. Such substituted amino acids can preferably be selected from one or more corresponding amino acids identified in a different coronavirus strain via a sequence alignment, such as shown above. For example, one or both underlined isoleucines can be substituted with leucine and/or methionine, as described in the alignment provided above. The underlined alanine can be substituted by valine, leucine or isoleucine. One or both underlined leucines can be independently substituted by isoleucine, tyrosine, alanine or valine. Other conservative or nonconservative substitutions, (lysine and glutamine or aspartic acid and glutamic acid) can be selected as well, for example, as shown in the above sequence alignment. In embodiments, amino acids that are conserved amongst 2, 3, 4, 5 or more coronavirus (e.g., coronavirus isolated from bats) remain conserved in the non-natural HRC peptide.

Modifications to wild type sequences are desirable. For example, using one or more D amino acids can improve pharmacokinetics and the half life of the peptide. Thus, the invention includes peptides characterized by 1, 2, 3, 4, 5, 6, 7, 8, 9, 10 or more D-amino acids. The D-amino acids can preferably be a corresponding L-amino acid of the wild type sequence. Preferably, the D-amino acid is an amino acid located at or near (e.g., within 1, 2, or 3 amino acids) a protease degradation site. Preferably, the D-amino acid is a hydrophobic amino acid participating in binding with the HRN peptide and preferably at a higher affinity than the corresponding wild type sequence. Alternatively or additionally, the D-amino acid is a hydrophilic amino acid, such as lysine, aspartic acid, glutamic acid or arginine. Alternatively or additionally, the D-amino acid can be selected from the 7 amino acids at the N-terminus of SEQ ID NO: 1.

However, swapping one or more D-amino acids for the corresponding L-amino acid can change the topology of the peptide and impact function. Therefore, a preferred non-natural HRC peptide is a Retro-Inversion HRC peptide, or "RI HRC peptide". Retro-Inversion HRC peptides are preferably characterized by a binding affinity of at least about 50% of the wild-type HRC peptide with its cognate ligand in a standard binding assay and decreased susceptibility to mammalian protease degradation. Retroinversion is defined as reversing a D-peptide sequence of a helical peptide or "flipping" the termini thereby restoring the presentation of the side chains to the binding ligand or target. See Kim et al, Method to generate highly stable D-amino acid analogs of bioactive helical peptides using a mirror image of the entire PBS, PNAS, Feb. 13, 2018 115 (7) 1505-1510, which is incorporated herein by reference in its entirety. Therefore, a non-natural peptide of the invention can include a peptide having the sequence of SEQ ID NO.: 1 wherein amino acids are D-amino acids, such as the amino acids within a region, flipping the N-terminus for a C terminus. For example, the N termini can be subjected to retroinversion as shown in SEQ ID NO. 2 where each D amino acid is preceded by a "d":

```
                                        (SEQ ID NO. 2)
dIdGdSdIdD NASVVNIQKEIDRLNEVAKNLNESLIDLQEL
```

This example offers a single RI region of 5 amino acids. However, as few as two amino acids can be selected (e.g., the 2 N-terminal amino acids). For example, the RI region can span the hydrophobic core, 1160N to 1176N, or the C-cap region or a portion thereof. Alternatively, the entire peptide can be an RI peptide. Additionally, two, three or more RI regions can be included. For example, both the N-terminus and C-Cap region can be RI regions, retaining the hydrophobic core with L-amino acids.

For example, in using mirror-image phage display to screen for HRC variants, a first D-peptide can be synthesized from a HRN coronavirus peptide, or first L-peptide. The first L-peptide can be a naturally occurring L-peptide or can be a chimera of a peptide. The methods can further comprise screening for a HRC peptide, or second L-peptide, that specifically binds to the first D-peptide; then, a second D-peptide that is the mirror image of the second L-peptide can be synthesized. In one aspect of the D-peptide screening methods described herein, an N-trimer target can first be synthesized with D-amino acids, creating the mirror image of the natural L-N-trimer target. The D-N-trimer target can be used in standard peptide-based screens such as phage display, ribosome display, and/or CIS display to identify L-peptides that bind to the D-N-trimer. The identified L-peptides can then be synthesized with D-amino acids. By the law of symmetry, the resulting D-peptides bind the natural L-N-trimer, and will thus target the N-trimer region of the coronavirus HRN intermediate, thereby inhibiting infection. This screening method is also described in Schumacher, et al., Identification of D-peptide ligands through mirror-image phage display, Science, 1996 Mar. 29; 271 (5257): 1854-7, which is hereby incorporated in its entirety by this reference.

Figure 3:
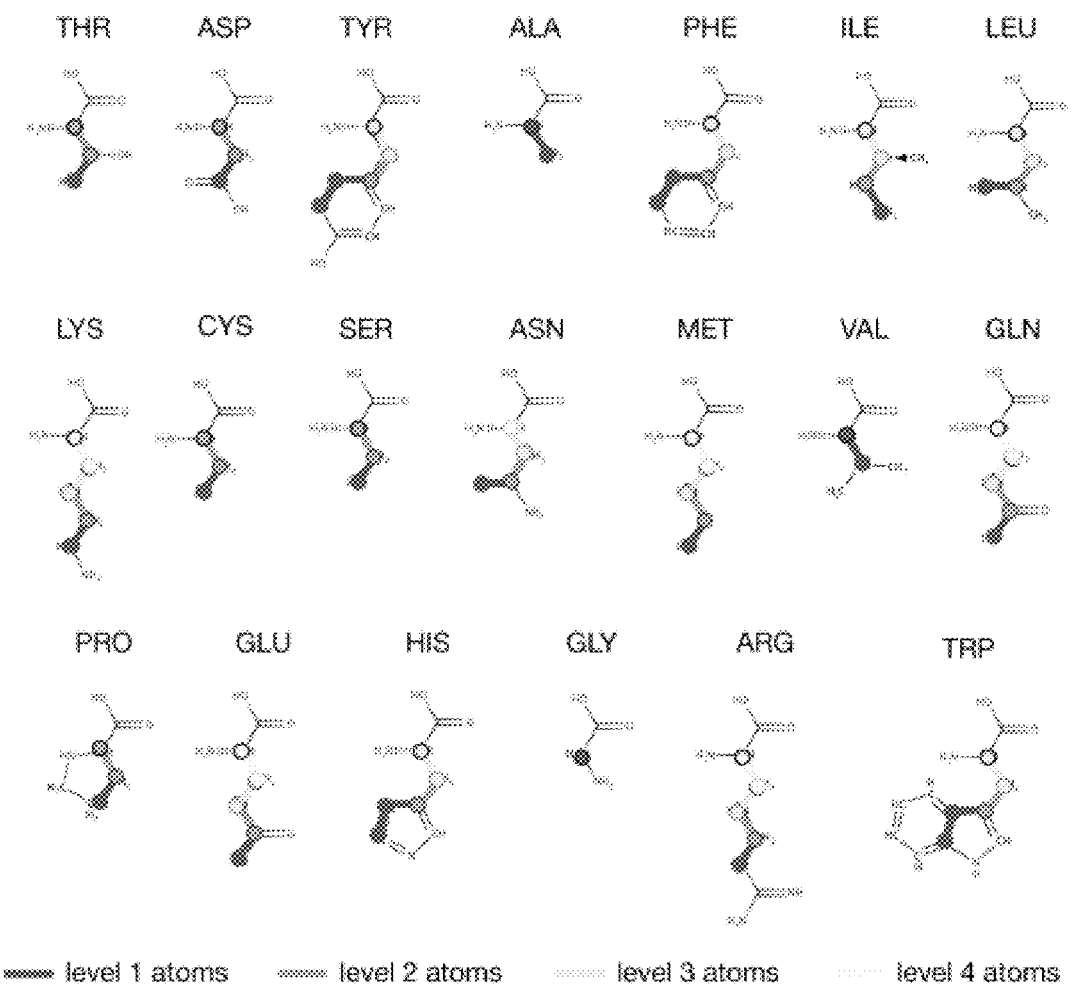
FIG. 3 illustrates atom rankings of various atoms in the amino acid sides chains.

FIG. 3 below provides default atom rankings for each amino acid, as described in Kim et al., 2017, which is hereby incorporated in its entirety by this reference.

The hotspot residues of the HRC peptide can be identified by crystal structure or NMR solution structure of the HRC peptide. For example, 1, 2, 3, 4, 5, 6, 7, 8, 9, 10 or more amino acids selected from 1150D, 1151I, 1154I, 1155N, 1158V, 1159V, 1161I, 1164E, 1171V, 1175L, 1176L, 1179L, 1180I, 1182L, 1184E and/or 1185Y, such as one or more amino acids selected from 1159V, 1160N, 1163E, 1171V, 1180I, 1184E and/or 1185L of SEQ ID NO. 1 can be designated hotspot residues.

The term "Linker" is defined as a bivalent moiety or group that covalently binds to a Peptide (preferably at the C or N terminus thereof) and to B. A Linker can have 1, 2, 3, 4, 5 or more subunits. For example, it can be advantageous to use a Linker with 3 subunits. A first optional subunit which comprises a flexible peptide, such as -(G)$_m$- or -(GS)$_m$G-, where m is an integer of 1, 2, 3, 4, 5 or more, such as 2. A second subunit can be a residue of a chemical reaction, such as a peptide bond, ester, ether, or thioether involving the N-terminus, C-terminus or side chain of the Peptide or first subunit. The residue can be non-cleavable, such as that formed with carbodiimide or sulfhydryl maleimide. A third optional subunit can be a hydrophilic spacer, such as polyethyleneglycol, polyethyleneamine, polyacetal polymer, poly (l-hydroxymethylethylene hydroxymethyl-formal) (PHF) or a carbohydrate. The hydrophilic spacers can generally be polymeric and comprise 1, 2, 3, 4, 5, 6, 7, 8, 9, 10 or more monomers. Polyethyleneglycol with 4 monomers (PEG4) is satisfactory. The length of the hydrophilic spacer can correspond to the span the S protein gap to facilitate the orientation of the peptide to bind the HRN domain. PEG can also reduce aggregation and improve solubility.

B is a multimeric core which covalently links each (Peptide-Linker) moiety to the hydrophobic moiety. Thus, where n is 2, B is a trivalent core. Where n is 3, B is quadravalent. Examples of trivalent cores include substituted trialkyl amines.

The Hydrophobic Moiety can be a membrane integrating lipid, such as cholesterol, a sphingolipid, sphingomyelin, a glycolipid, glycerophospholipid (such as phosphatidylcholine, phosphatidylethanolamine and phosphatidylserine), ergosterol, 7-dihydrocholesterol and stigmasterol. preferably cholesterol. Typically, B is linked directly or indirectly to a cholesterol hydroxyl group, such as 3-OH. The hydrophobic moiety facilitates insertion of the compound of the invention into a cell membrane and can inhibit viral entry.

Phospholipids include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the I position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the formulations can include dipalmitoylphosphatidylcholine (DPPC), a major constituent of naturally-occurring lung surfactant. Other examples include dimyristoylphosphatidylcholine (DMPC) and dimyristoylphosphatidylglycerol (DMPG) dipalmitoylphosphatideholine (DPPQ) and dipalmitoylphosphatidylglycerol (DPPG) distearoylphosphatidylcholine (DSPQ) and distearoylphosphatidylglycerol (DSPG), dioleylphosphatidylethanolamine (DOPE) and mixed phospholipids like palmitoylstearoylphosphatidyl-choline (PSPC) and palmitoylstearoylphosphatidylglycerol (PSPG), and single acylated phospholipids like mono-oleoyl-phosphatidylethanolamine (MOPE).

Cholesterols can include, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hemi-succinates, salts of tocopherols including tocopherol hydrogen sulfates and tocopherol sulfates.

The compositions of the invention comprise a compound as described herein and a pharmaceutically acceptable carrier. For example, the composition can be administered systemically or locally. The composition can be administered for oral, intravenous, intramuscular, rectal, cutaneous, subcutaneous, topical, transdermal, sublingual, nasal, inhalation, or vaginal delivery, for example. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The compositions may be formulated according to conventional pharmaceutical practice (see, e.g., Remington: The Science and Practice of Pharmacy, 22nd edition, 2013, ed. L. V. Allen, Pharmaceutical Press, Philadelphia, and Encyclopedia of Pharmaceutical Technology, 4.sup.th Edition, ed. J. Swarbrick, 2013, CRC Press, New York).

Compounds may be formulated in a variety of ways that are known in the art. For example, one or more compounds of the invention and any additional biologically active agent, if present, as defined herein may be formulated together or separately.

Each compound of the invention, alone or in combination with one or more active agents as described herein, can be formulated for controlled release (e.g., sustained or measured) administration, as described in U.S. Patent Application Publication Nos. 2003/0152637 and 2005/0025765, each incorporated herein by reference. For example, a compound of the invention, alone or in combination with one or more of the biologically active agents as described herein, can be incorporated into a capsule or tablet that is administered to the patient.

Controlled release formulations known in the art include specially coated pellets, polymer formulations or matrices for surgical insertion or as sustained release microparticles, e.g., microspheres or microcapsules, for implantation, insertion, infusion or injection, wherein the slow release of the active medicament is brought about through sustained or controlled diffusion out of the matrix and/or selective breakdown of the coating of the preparation or selective breakdown of a polymer matrix. Other formulations or vehicles for controlled, sustained or immediate delivery of an agent to a preferred localized site in a patient include, e.g., suspensions, emulsions, gels, liposomes and any other suitable art known delivery vehicle or formulation acceptable for subcutaneous or intramuscular administration.

Suitable biocompatible polymers can be utilized as the controlled release material. The polymeric material may comprise biocompatible, biodegradable polymers, and, in certain preferred embodiments, is preferably a copolymer of lactic and glycolic acid. Preferred controlled release materials which are useful in the formulations of the invention include the polyanhydrides, polyesters, co-polymers of lactic acid and glycolic acid (preferably wherein the weight ratio of lactic acid to glycolic acid is no more than 4:1 i.e., 80% or less lactic acid to 20% or more glycolic acid by weight) and polyorthoesters containing a catalyst or degradation enhancing compound, for example, containing at least 1% by weight anhydride catalyst such as maleic anhydride. Examples of polyesters include polylactic acid, polyglycolic acid and polylactic acid-polyglycolic acid copolymers. Other useful polymers include protein polymers such as collagen, gelatin, fibrin and fibrinogen and polysaccharides such as hyaluronic acid.

In additional embodiments, the controlled release material, which in effect acts as a carrier for a compound of the invention can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan. In embodiments where the biodegradable polymer comprises a gel, one such useful polymer is a thermally gelling polymer, e.g., polyethylene oxide, polypropylene oxide (PEO-PPO) block copolymer such as PLURONIC™ F127 from BASF Wyandotte.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, taste masking agents (such as hydroxypropyl methylcellulose, hydroxypropyl cellulose) and the like.

One or more compounds of the invention may be mixed together in a tablet, capsule, or other vehicle, or may be partitioned. In one example, a compound of the invention is contained on the inside of the tablet, and the biologically active agent is on the outside of the tablet, such that a substantial portion of the biologically active agent is released prior to the release of the compound of the invention.

Formulations for oral use may also be provided as chewable tablets, or as hard gelatin capsules wherein the active ingredient(s) are mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment. Formulations to the mouth may also be provided as a mouthwash, an oral spray, oral rinse solution, or oral ointment, or oral gel.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

Liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

The composition of the invention can comprise a liquid vehicle which is suitable for nasal administration. The vehicle is preferably an aqueous solution. More preferably, the vehicle is an aqueous solution which includes a viscosity enhancing agent and, optionally one or more additional excipients which, for example, improve formulation stability and/or comfort upon administration.

A variety of viscosity enhancing agents are known in the art. Viscosity enhancing agents include hydrophilic polymers, such as polysaccharides, polysaccharide derivatives, proteins and synthetic polymers. Examples include, but are not limited to, acacia, tragacanth, alginic acid, carrageenan, locust bean gum, guar gum, gelatin, hyaluronic acid, polyacrylate, polyacrylate/alkylacrylate copolymers, polyvinyl alcohol, polyvinylpyrrolidone, starch, propylene glycol alginate, maltodextrin, and cellulose ether derivatives, such as methylcellulose, hydroxyethylcellulose, hydroxypropylmethylcellulose, hydroxypropylcellulose, and carboxymethylcellulose. Where possible, salt forms of any of the foregoing are preferred. Preferred viscosity enhancing agents include hyaluronic acid, including sodium hyaluronate; carboxymethylcellulose, including sodium carboxymethylcellulose and calcium carboxymethylcellulose; methylcellulose, hydroxyethylcellulose, hydroxypropylmethylcellulose, and hydroxypropylcellulose.

The composition optionally includes one or more additional excipients which, for example, increase the ease of administration, the comfort of the subject, or the stability of the composition. Suitable additional excipients include, but are not limited to, tonicity modifiers, such as sodium chloride and dextrose; antioxidants, such as butylated hydroxyanisole; buffers, such as sodium bicarbonate, sodium citrate and sodium phosphate; preservatives, such as benzalkonium chloride, ethanol, propylene glycol, benzoyl alcohol, phenethyl alcohol, chlorobutanol or methylparaben; pH adjusters, such as hydrochloric acid, sulfuric acid and sodium hydroxide; surfactants, such as Polysorbate 80, Polysorbate 20, and polyoxyl 400 stearate; chelating agents, such as disodium EDTA; antioxidants; co-solvents, such as ethanol, PEG 400, and propylene glycol; penetration enhancers, such as oleic acid; and humectants, such as glycerin (see S. Thorat, Sch. J. App. Med. Sci. 2016, 4 (8D): 2976-2985; D. Marx et al., "*Intranasal Drug Administration—An Attractive Delivery Route for Some Drugs*," IntechOpen, DOI: 10.5772/59468.

In one embodiment, the vehicle consists of sodium hyaluronate, aloe vera, allantoin, sodium chloride, sodium bicarbonate, glycerin, propylene glycol, propylene glycol, benzalkonium chloride and USP grade purified water. A suitable vehicle is sold by NeilMed™ under the tradename NasoGEL™.

The amount of active agent in the composition can vary, for example, from about 0.5% by weight to about 25% by weight.

The pH of the formulation is tolerable in the nasal cavity and preferably at least about 8.0. Buffers that can be used in the formulation include, but are not limited to phosphate, TRIS, [tris (hydroxymethyl) methylamino] propanesulfonic acid, 2-(bis(2-hydroxyethyl) amino) acetic acid, and N-[tris (hydroxymethyl) methyl]glycine, and Alkaline Buffer (Seachem).

A pharmaceutical composition suitable for nasal or pulmonary administration comprising a water-soluble solvent selected from the group consisting of propylene glycol, glycerin, polyethylene glycol, and combinations thereof. The composition can further comprise one or more of a polysaccharide gum, a non-ionic surfactant, and a preservative. An exemplary polysaccharide gum is sclerotium gum. Exemplary surfactants are poloxamers, including, but not limited, to poloxamer 188. The preservative can, for example, be benzalkonium chloride.

The composition can be a dry powder and delivered by a dry powder inhaler, suspended in a propellant or in an aqueous suspension or solution and delivered via a nebulizer.

For example, a solution or suspension of the active agent and a pulmonary excipient, such as lactose, can be spray dried to form particles having a fine particle fraction sufficient to deliver to the lungs or upper respiratory system. Alternatively, an aqueous solution or suspension can be sonicated, thereby aerosolizing the solution/suspension to a droplet size that can be inhaled, e.g., via a nebulizer.

Excipients include carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Other excipients suitable for use with the present invention, including amino acids, are known in the art such as those disclosed in WO 95/31479, WO 96/32096, and WO 96/32149. Mixtures of carbohydrates and amino acids are further held to be within the scope of the present invention. The inclusion of both inorganic (e.g., sodium chloride, etc.), organic acids and their salts (e.g., carboxylic acids and their salts such as sodium citrate, sodium ascorbate, magnesium gluconate, sodium gluconate, tromethamine hydrochloride, etc.) and buffers is also contemplated.

The compositions may be used in the form of dry powders or in the form of stabilized dispersions comprising a non-aqueous phase. Accordingly, the dispersions or powders of the present invention may be used in conjunction with metered dose inhalers (MDIs), dry powder inhalers (DPIs), atomizers, nebulizers or liquid dose instillation (LDI) techniques to provide for effective drug delivery. With respect to inhalation therapies, those skilled in the art will appreciate that the hollow and porous microparticles of the present invention are particularly useful in DPIs. Conventional DPIs comprise powdered formulations and devices where a predetermined dose of medicament, either alone or in a blend with lactose carrier particles, is delivered as an aerosol of dry powder for inhalation.

The medicament is formulated in a way such that it readily disperses into discrete particles with a mass median aerodynamic diameters of the powders will characteristically range from about 0.5-10, preferably from about 0.5-5.0 microns MMAD.

As discussed above, the stabilized dispersions disclosed herein may also be administered to the nasal or pulmonary air passages of a patient via aerosolization, such as with a metered dose inhaler. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being within the scope thereof. However, it should be emphasized that, in preferred embodiments, the stabilized dispersions may be administered with an MDI using a number of different routes including, but not limited to, topical, nasal, pulmonary or oral. Those skilled in the art will appreciate that, such routes are well known and that the dosing and administration procedures may be easily derived for the stabilized dispersions of the present invention.

Along with the aforementioned embodiments, the stabilized dispersions of the present invention may also be used in conjunction with nebulizers as disclosed in PCT WO 99/16420, the disclosure of which is hereby incorporated in its entirety by reference, in order to provide an aerosolized medicament that may be administered to the pulmonary air passages of a patient in need thereof. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being within the scope thereof.

Along with DPIs, MDIs and nebulizers, it will be appreciated that the stabilized dispersions of the present invention may be used in conjunction with liquid dose instillation or LDI techniques as disclosed in, for example, WO 99/16421 hereby incorporated in its entirety by reference. Liquid dose instillation involves the direct administration of a stabilized dispersion to the lung. In this regard, direct pulmonary administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

Methods of Use

The invention also includes methods of using the composition of the invention for treating or preventing an infection in a subject in need thereof. The method comprises the step of administering an effective amount of the composition to the subject. The infection can be an infection of the gastrointestinal tract or upper or lower respiratory tract, including the common cold, influenza, respiratory syncytial virus infection, Severe Acute Respiratory Syndrome, Middle East Respiratory Syndrome, COVID-19 or a disease caused by another emerging zoonotic virus, such as a zoonotic coronavirus. In specific aspects, the methods of the invention treat a viral respiratory infection, such as a SARS-COV-2 (COVID-19) respiratory infection.

The subject, preferably a human, can be an individual diagnosed with the infection and is either symptomatic, pre-symptomatic, or asymptomatic, or at risk for developing infection. For example, the subject can be at risk for developing the viral respiratory infection due to direct or indirect exposure or possible exposure to the virus (such as SARS-COV-2 or a mutant thereof), such as via exposure to an infected individual or a virus-contaminated fomite. The subject can be a resident of, or a visitor to, a community in which the viral respiratory infection has been identified, for example, the subject can be a family member of an infected individual or the subject can work in a health care setting caring for infected individuals. In certain embodiments, the subject at risk for infection is asymptomatic and has tested negative for presence of the virus prior to the commencement of therapy. In specific examples, the subject can be at risk for developing COVID-19 due to exposure to the SARS-COV-2 virus, for example, from the respiratory droplets or aerosols of an infected individual and/or contact with a contaminated fomite. In yet further aspects, the subject is suffering from COVID-19 including subjects suffering from mild, moderate or severe COVID-19.

In certain embodiments of the method of the invention, the subject suffers from another disease or condition, such as chronic obstructive pulmonary disease (COPD) or ulcerative colitis, which can be exacerbated by an infection.

The composition is preferably administered to the subject before the subject is symptomatic (e.g., pre-symptomatic), or at the onset of symptoms. The composition can be administered at a variety of dosing schedules. For example, the composition can be administered one or more times and over a course of one or more days. In certain embodiments, the composition is administered one or more times per day for one to 10 days. In certain embodiments, the composition is administered one or more times per day until the subject is asymptomatic and/or testing for the virus is negative.

The composition can be administered to the nasal passages using routine methods and devices (see D. Marx et al., "*Intranasal Drug Administration—An Attractive Delivery Route for Some Drugs,*" IntechOpen, DOI: 10.5772/59468. For example, the composition can be administered to the nasal passages as drops or as an aerosol spray, for example, using an aerosol bottle or a multi-dose spray pump, which can provide a uniform metered dose. The volume per dose can be varied, but is typically from about 50 to about 150 µl. The desired volume will depend on the desired dose of the active agent and the concentration of the active agent in the composition.

Where delivery to the pulmonary system, or lungs, is desired it can be efficacious to aerosolize a low concentration solution of the active agent for an extended period, such as overnight.

Combination Therapies

The product or composition can be co-administered with other active agents and therapies.

The active agents and compositions of the present invention are also intended for use with general care provided patients with viral infections, including parenteral fluids (including dextrose saline and Ringer's lactate) and nutrition, antibiotic (including metronidazole and cephalosporin antibiotics, such as ceftriaxone and cefuroxime) and/or antiviral prophylaxis, fever (e.g., acetaminophen) and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such as artemether, artesunate-lumefantrine combination therapy), quinolone antibiotics, such as ciprofloxacin, macrolide antibiotics, such as azithromycin, cephalosporin antibiotics, such as ceftriaxone, or aminopenicillins, such as ampicillin), or shigellosis.

The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents and/or as part of the same treatment regimen. For example, a unit dose of a compound of the invention can be administered first, followed within seconds or minutes or days by administration of a unit dose of one or more other active therapeutic agents. Alternatively, a unit dose of one or more other therapeutic agents can be administered first, followed by administration of a unit dose of a compound of the invention within seconds or minutes or days. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic," i.e., the effect achieved when the active ingredients used together is greater than the sum of the effects that results from using the compounds separately.

As used herein, the words "a" and "an" are meant to include one or more unless otherwise specified. For example, the term "an agent" encompasses both a single agent and a combination of two or more agents.

The term "treating" or "treatment" as used herein covers the treatment of the disease or condition of interest (e.g., a respiratory infection) in a mammal, preferably a human, having the disease or condition of interest, and includes, for example: preventing or delaying the onset of the disease or condition from occurring in a mammal, in particular, when such mammal is at risk of developing the disease but has not yet become symptomatic and/or been diagnosed as having it; inhibiting the disease or condition, i.e., arresting its development; relieving the disease or condition, i.e., causing regression of the disease or condition; and/or stabilizing the disease or condition. Treatment includes ameliorating or lessening the severity of symptoms of the disease or condition, and/or inhibition of further progression or worsening of those symptoms. Treatment also includes shortening the time course and/or severity of a disease or condition compared to the expected or historical time course and/or severity of the disease.

As used herein the terms "preventing," means causing the clinical symptoms of a disease or condition not to develop and includes inhibiting the onset of a viral infection in a subject that may be exposed to or predisposed to the viral infection but does not yet experience or display symptoms of the infection.

An "effective amount" or a "therapeutically effective amount" of a compound or composition described herein refers to an amount of the compound that is sufficient to achieve a specific effect or result, and/or prevents or treats the disease or condition and/or the symptoms therefore, for example, alleviating, in whole or in part, symptoms associated with the disorder or condition, or halts or slows further progression or worsening of those symptoms, or prevents or provides prophylaxis for the disorder or condition. The "effective amount" and "therapeutically effective amount" includes specifically an anti-viral amount of a compound of the invention (alone or in combination with another active agent) or the composition described herein.

The invention is illustrated by the following examples which are not meant to be limiting in any way.

While this invention has been particularly shown and described with references to preferred embodiments thereof, it will be understood by those skilled in the art that various changes in form and details may be made therein without departing from the scope of the invention encompassed by the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. The relevant teachings of all patents, published applications and references cited herein are incorporated by reference in their entirety.

What is claimed is:

1. A compound having the formula:

(Peptide-Linker)$_n$-B-Hydrophobic Moiety wherein said Peptide is a non-native C-terminus heptad repeat region (HRC) Peptide that comprises the sequence of:

(SEQ ID NO. 2)
dIdGdSdIdD NASVVNIQKEIDRLNEVAKNLNESLIDLQEL, wherein the dIdGdSdIdD represents that the first five amino acids of said sequence are in the D-configuration;

said Linker is a bivalent linking moiety,

B is a multivalent moiety and n is an integer selected from 1, 2, and 3.

2. The compound of claim 1, wherein the Hydrophobic moiety is cholesterol.

3. A method for the treatment of a disease associated with severe acute respiratory syndrome coronavirus type 2 (SARS-COV-2) infection in a subject in need thereof, wherein the method comprises administering to the subject an effective amount of the compound of claim 2.

4. The method of claim 3, wherein the administration is achieved using an inhaler or a nebulizer.

5. The compound of claim 1, wherein the Linker comprises a flexible peptide.

6. The compound of claim 1, wherein the Linker comprises a polyethyleneglycol.

7. The compound of claim 1, wherein n is 2.

* * * * *